United States Patent
Carls et al.

(10) Patent No.: US 12,004,910 B2
(45) Date of Patent: Jun. 11, 2024

(54) SURGICAL SYSTEM AND METHOD

(71) Applicant: WARSAW ORTHOPEDIC INC., Warsaw, IN (US)

(72) Inventors: Thomas A. Carls, Memphis, TN (US); Newton H. Metcalf, Jr., Memphis, TN (US); Richard L. Brown, Mesa, AZ (US); Jason M. May, St. Johns, FL (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 17/151,475

(22) Filed: Jan. 18, 2021

(65) Prior Publication Data

US 2021/0161609 A1 Jun. 3, 2021

Related U.S. Application Data

(63) Continuation of application No. 16/405,576, filed on May 7, 2019, now Pat. No. 10,893,915.

(51) Int. Cl.
*A61B 90/00* (2016.01)
*A61B 17/70* (2006.01)
(Continued)

(52) U.S. Cl.
CPC .......... *A61B 90/06* (2016.02); *A61B 17/7032* (2013.01); *A61B 17/7037* (2013.01);
(Continued)

(58) Field of Classification Search
CPC ................ A61B 90/06; A61B 17/7037; A61B 2017/00221; A61B 2017/564;
(Continued)

(56) References Cited

U.S. PATENT DOCUMENTS 5,470,354 A   11/1995   Hershberger et al.
6,280,445 B1   8/2001   Morrison et al.
(Continued)

FOREIGN PATENT DOCUMENTS

WO   2015200720 A2   12/2015
WO   2017007821 A1   1/2017
WO   2017165717 A1   9/2017

OTHER PUBLICATIONS

Korean Intellectual Property Office, Republic of Korea, Patent Cooperation Treaty, the International Search Report and the Written Opinion of the International Searching Authority, International application No. PCT/US2019/042511, dated Oct. 31, 2019.
(Continued)

*Primary Examiner* — Julianna N Harvey
(74) *Attorney, Agent, or Firm* — Sorell, Lenna & Schmidt, LLP

(57) ABSTRACT

A spinal construct includes a first member having a first thread form and an implant cavity configured for disposal of the spinal implant. A second member is engageable with a spinal implant and includes a second thread form configured for engagement with the first thread form. A gauge is coupled to the second member. The gauge is configured to measure a force between the second member and the spinal implant when the second member is engaged with the first member. The second thread form is timed with the first thread form to position the gauge in a selected orientation relative to the spinal implant. Systems and methods are disclosed.

18 Claims, 5 Drawing Sheets

(51) Int. Cl.
  *A61B 17/00* (2006.01)
  *A61B 17/56* (2006.01)
(52) U.S. Cl.
  CPC ............... *A61B 2017/00221* (2013.01); *A61B 2017/564* (2013.01); *A61B 2090/065* (2016.02)
(58) Field of Classification Search
  CPC .................. A61B 2090/064–2090/065; A61B 17/7032–17/704; A61B 17/86–17/8695
  See application file for complete search history.

(56) References Cited

U.S. PATENT DOCUMENTS

| | | | |
|---|---|---|---|
| 7,976,547 B2 | 7/2011 | Vendrely et al. | |
| 9,220,540 B2 | 12/2015 | Biedermann et al. | |
| 2005/0267477 A1 | 12/2005 | Jackson | |
| 2006/0052782 A1* | 3/2006 | Morgan | A61B 17/80 606/60 |
| 2006/0149235 A1* | 7/2006 | Jackson | A61B 17/7032 606/1 |
| 2008/0281212 A1 | 11/2008 | Nunez et al. | |
| 2009/0234391 A1 | 9/2009 | Butler et al. | |
| 2010/0201118 A1* | 8/2010 | Anton | F16L 19/086 285/382.7 |
| 2012/0215263 A1* | 8/2012 | Lee | A61B 17/8685 606/305 |
| 2014/0125482 A1* | 5/2014 | Rigsby | A61L 2/00 340/539.13 |
| 2017/0196508 A1* | 7/2017 | Hunter | A61B 17/7059 |
| 2018/0195547 A1* | 7/2018 | Demeocq | G01L 5/24 |

OTHER PUBLICATIONS

Korean Intellectual Properly Office Republic of Korea, Patent Cooperation Treaty, the International Search Report and the Written Opinion of the International Searching Authority, International application No. PCT/US2019/042513, dated Oct. 31, 2019.

Korean Intellectual Properly Office Republic of Korea, Patent Cooperation Treaty, the International Search Report and the Written Opinion of the International Searching Authority, International application No. PCT/US2020/042516, dated Oct. 31, 2019.

Korean Intellectual Properly Office Republic of Korea, Patent Cooperation Treaty, the International Search Report and the Written Opinion of the International Searching Authority, International application No. PCT/US2020/041487, dated Nov. 2, 2020.

China National Intellectual Property Administration-Cnipa, Notice of the First Office Action, Application/Patent No. 202010348764.5, Date of Dispatch Oct. 28, 2023.

* cited by examiner

SURGICAL SYSTEM AND METHOD

CROSS REFERENCE TO RELATED APPLICATIONS

This application is a continuation of U.S. patent application Ser. No. 16/405,576, filed May 7, 2019, which is expressly incorporated by reference herein, in its entirety.

TECHNICAL FIELD

The present disclosure generally relates to medical devices for the treatment of musculoskeletal disorders, and more particularly to a surgical system and a method for treating a spine.

BACKGROUND

Spinal pathologies and disorders such as scoliosis, kyphosis and other curvature abnormalities, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support vertebral members. During surgical treatment, one or more rods and bone fasteners can be delivered to a surgical site. The rods may be attached via the fasteners to the exterior of two or more vertebral members. Setscrews can be used to secure the rods with the fasteners. However, the connection force and continued integrity of the connection between the rods and the fasteners can be challenging to monitor during and after implantation. In addition, it is difficult to monitor that a proper or acceptable force is maintained between the setscrews and the rods. This disclosure describes an improvement over these prior technologies.

SUMMARY

In one embodiment, a spinal construct is provided. The spinal construct includes a first member. The first member comprises a first thread form and an implant cavity configured for disposal of a spinal implant. A second member is engageable with the spinal implant. The second member comprises a second thread form configured for engagement with the first thread form. A gauge is coupled to the second member. The gauge is configured to measure a force between the second member and the spinal implant when the second member is engaged with the first member. The second thread form is timed and/or clocked with the first thread form to position the gauge in a selected orientation relative to the spinal implant.

In one embodiment, a surgical method is provided that includes: coupling a first member to tissue; positioning a spinal implant in an implant cavity of the first member; and engaging a first thread form of the first member with a second thread form of a second member such that the second member applies a force to the spinal implant, wherein the second member comprises a gauge, and wherein the second thread form is timed and/or clocked with the first thread form to position the gauge in a selected orientation relative to the spinal implant.

In one embodiment, a spinal construct is provided. The spinal construct includes a bone screw. The bone screw comprises a pair of arms. The arms define a U-shaped implant cavity configured for disposal of a spinal rod. Inner surfaces of the arms define a first thread form. A setscrew is engageable with the spinal rod. The setscrew comprises an inner surface and an outer surface. The inner surface of the setscrew defines a socket. The outer surface defines a second thread form configured for engagement with the first thread form. A gauge is positioned within the socket. The gauge is configured to measure a force between the setscrew and the spinal rod when the setscrew is engaged with the bone screw. The second thread form is timed and/or clocked with the first thread form to position the gauge in a selected orientation relative to the spinal rod.

BRIEF DESCRIPTION OF THE DRAWINGS

The present disclosure will become more readily apparent from the specific description accompanied by the following drawings, in which.

DETAILED DESCRIPTION

Figure 1:
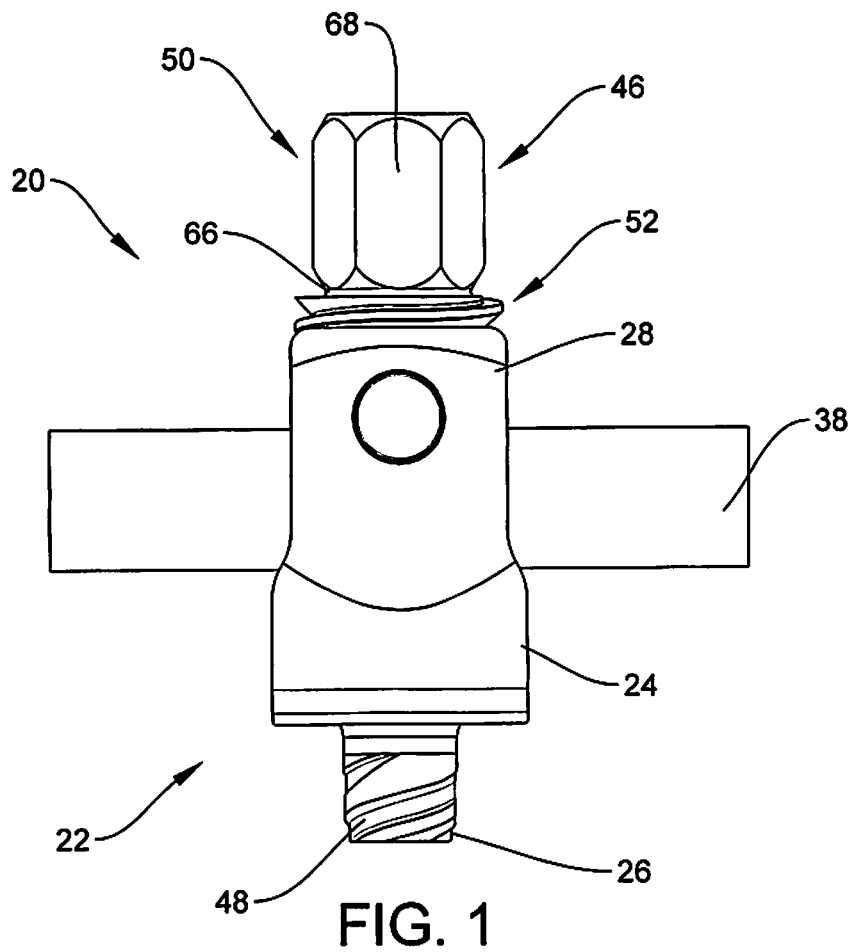
FIG. 1 is a side view of components of one embodiment of a surgical system, in accordance with the principles of the present disclosure.

The exemplary embodiments of the surgical system and related methods of use disclosed are discussed in terms of medical devices for the treatment of musculoskeletal disorders and more particularly, in terms of a surgical system and a method for treating a spine. In some embodiments, the systems and methods of the present disclosure comprise medical devices including surgical instruments and implants that are employed with a surgical treatment, as described herein, for example, with a cervical, thoracic, lumbar and/or sacral region of a spine.

In some embodiments, the present surgical system comprises the ability to collect data from a fixation implant to allow surgeons to monitor the implant status and/or fusion state. In some embodiments, gauge s, such as, for example, strain gauges, are placed on the implants to collect and transmit data intra-operatively and post-operatively. The gauge s can detect loading conditions of the implanted construct. The orientation of the gauge is controlled to avoid variable loading detection.

In some embodiments, the implant construct contains a pedicle screw, rod, and setscrew. The setscrew contains gauge s, such as, for example, strain gauges, which detect loading. The thread on the setscrew and pedicle screw are timed and/or clocked to allow consistent orientation once the setscrew is locked. Gauges are mounted in a controlled orientation with respect to the start of the setscrew thread. This allows orientation of the gauge s to be controlled with respect to the rod. It is envisioned that the number and configuration of gauge s may vary, as discussed herein.

In some embodiments, the present surgical system allows loading data to be captured from an implant. The control of the orientation ensures reproducibility in the measurements. In some embodiments, gauge orientation is controlled with respect to the thread start of the setscrew. In some embodiments, the thread start of the setscrew defines a controlled dimension of the setscrew. In some embodiments, the setscrew includes an inner surface that defines a socket, the gauge being applied to the inner surface. In some embodiments, the gauge orientation is controlled such that the gauge orientation is inline with an orientation of a rod. In some embodiments, the gauge orientation is controlled such that the gauge orientation is transverse to the orientation of a rod. In some embodiments, the gauge orientation is controlled such that the gauge orientation is non-parallel (e.g., at an acute angle) relative the orientation of a rod. In some embodiments, the system includes a tulip head having threads that are timed and/or clocked to a rod slot of the tulip.

In some embodiments, the surgical system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues;

as an adjunct in surgery; and/or any repair procedure. In some embodiments, as used in the specification and including the appended claims, the term "tissue" includes soft tissue, ligaments, tendons, cartilage and/or bone unless specifically referred to otherwise.

The following discussion includes a description of a surgical system including a surgical instrument, implants, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-12, there are illustrated components of a surgical system, such as, for example, a surgical system 20.

The components of surgical system 20 can be fabricated from biologically acceptable materials suitable for medical applications, including metals, synthetic polymers, ceramics and bone material and/or their composites. For example, the components of surgical system 20, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of surgical system 20 may have material composites, including the above materials, to achieve various desired characteristics such as strength, rigidity, elasticity, compliance, biomechanical performance, durability and radiolucency or imaging preference. The components of surgical system 20, individually or collectively, may also be fabricated from a heterogeneous material such as a combination of two or more of the above-described materials. The components of surgical system 20 may be monolithically formed, integrally connected or include fastening elements and/or instruments, as described herein.

Surgical system 20 is employed, for example, with a fully open surgical procedure, a minimally invasive procedure including percutaneous techniques, and mini-open surgical techniques to deliver and introduce instrumentation and/or one or more spinal implants, such as, for example, one or more components of a bone fastener, at a surgical site of a patient, which includes, for example, a spine. In some embodiments, the spinal implant can include one or more components of one or more spinal constructs, such as, for example, interbody devices, interbody cages, bone fasteners, spinal rods, tethers, connectors, plates and/or bone graft, and can be employed with various surgical procedures including surgical treatment of a cervical, thoracic, lumbar and/or sacral region of a spine.

Surgical system 20 includes a first member, such as, for example, a bone screw 22 including a head, such as, for example, a tulip head 24 and a shaft 26 configured to be connected with head 36, as discussed herein. Head 24 includes a pair of spaced-apart arms 28, 30. Arm 28 includes an inner surface 32 and arm 30 includes an inner surface 34. Surfaces 32, 34 define a U-shaped passageway, such as, for example, an implant cavity 36. Cavity 36 is configured for disposal of a spinal implant, such as, for example, a spinal rod 38. In some embodiments, all or only a portion of cavity 36 may have alternate cross section configurations, such as, for example, oval, oblong, triangular, square, polygonal, irregular, uniform, non-uniform, offset, staggered, and/or tapered. In some embodiments, arms 28, 30 may be disposed at alternate orientations, relative to a longitudinal axis of screw 22, such as, for example, transverse, perpendicular and/or other angular orientations such as acute or obtuse, co-axial and/or may be offset or staggered. Arm 28 includes a thread 40 and arm 30 includes a thread 42 that faces thread 40. Threads 40, 42 define a first thread form 44 configured for engagement with a thread form of a second member, such as, for example, a setscrew 46 to fix rod 38 relative to head 24, as discussed herein. In some embodiments, setscrew 46 can be made, sold, or provided with independently from one or both of screw 22 and rod 38.

Shaft 26 has a cylindrical cross-sectional configuration and includes an outer surface having an external thread form 48. In some embodiments, thread form 48 may include a single thread or a plurality of discrete threads. In some embodiments, other engaging structures may be located on shaft 26, such as, for example, a nail configuration, barbs, expanding elements, raised elements and/or spikes to facilitate engagement of shaft 26 with tissue.

In some embodiments, all or only a portion of shaft 26 may have alternate cross section configurations, such as, for example, oval, oblong, triangular, square, polygonal, irregular, uniform, non-uniform, offset, staggered, undulating, arcuate, variable and/or tapered. In some embodiments, the outer surface of shaft 26 may include one or a plurality of openings. In some embodiments, all or only a portion of the outer surface of shaft 26 may have alternate surface configurations to enhance fixation with tissue, such as, for example, rough, arcuate, undulating, mesh, porous, semi-porous, dimpled and/or textured. In some embodiments, all or only a portion of shaft 26 may be disposed at alternate orientations, relative to its longitudinal axis, such as, for example, transverse, perpendicular and/or other angular orientations such as acute or obtuse, co-axial and/or may be offset or staggered. In some embodiments, all or only a portion of shaft 26 may be cannulated.

Setscrew 46 comprises an upper portion 50 and a lower portion 52. Portion 52 includes a second thread form 54 that extends outwardly from an outer circumferential surface of portion 52. Thread form 54 is configured to mate with thread form 44 to fix rod 38 relative to head 24, as discussed herein. Portion 50 has a length and width that is configured to facilitate manipulation of setscrew 46. A bottom tip 56 is formed on a bottom end 58 of setscrew 46 and is located centrally on bottom end 58 so as to extend outward along a central longitudinal axis X of rotation of setscrew 46. Setscrew 46 is configured to exert a compression or clamping force onto rod 38 through tip 56. In particular, tip 56 impinges on rod 38 and may, in some embodiments, form a dimple or depression in rod 38. In some embodiments, tip 56 is substantially dome shaped with a surface that is convex or rounded so that a small surface area is in contact with rod 38 providing a strong grip when pressed against rod 38. Alternatively, in some embodiments, tip 56 could be of various shaped points including flat, cone, cup, dog, or knurled. In some embodiments, portion 50 has a hexagonal external cross-section and round internal cross-section. In some embodiments, the internal cross-section of portion 50 and/or the external cross-section of portion 50 can be variously shaped, such as, for example, circular, oval, oblong, triangular, square, polygonal, irregular, uniform, non-uniform, offset, staggered, undulating, arcuate, variable and/or tapered.

In some embodiments, an inner surface 60 of setscrew 46 defines a hollow bore, such as, for example, a socket 62 in the body of setscrew 46. Socket 62 extends from an opening in portion 50 and, in various embodiments, into at least a section of portion 52. The section of socket 62 extending into portion 52 comprises a driving recess 64 for assisting in the removal by internal wrenching of portion 52 after portion 50 has been broken away at a frangible portion 66, as discussed herein. In some embodiments, recess 64 has a shape that can be a hexagon, hexalobular, clutch, fluted, frearson, slotted, star, Torx, reverse thread, Pozidriv, or Phillips.

Figure 10:
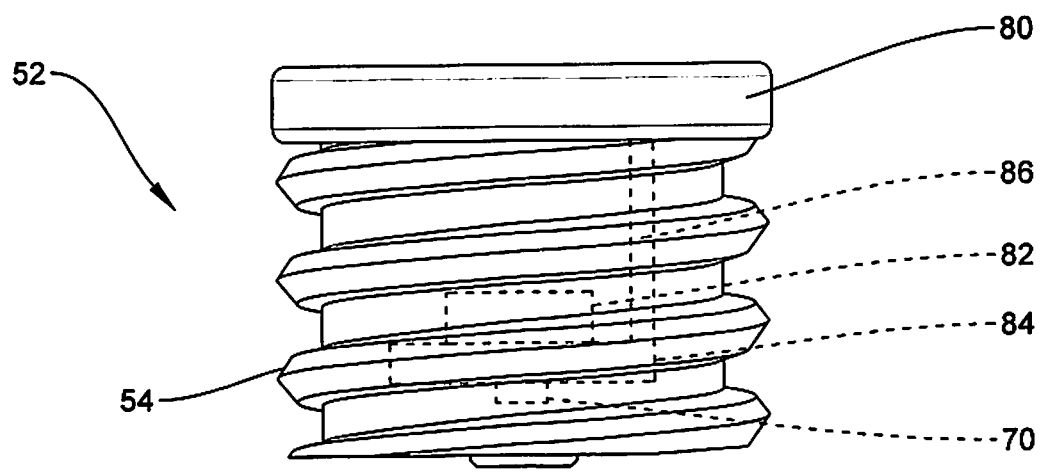
FIG. 10 is a side view of the second component shown in FIG. 4, the third component shown in FIG. 9, the fourth component shown in FIG. 9, the fifth component shown in FIG. 9, the sixth component shown in FIG. 9, and the seventh component shown in FIG. 9.
Figure 11:
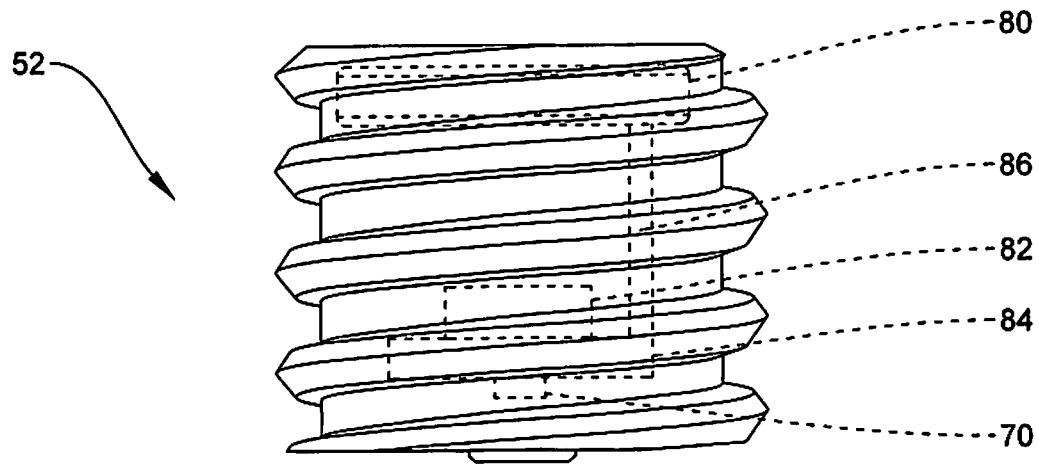
FIG. 11 is a side view of the second component shown in FIG. 4, the third component shown in FIG. 9, one embodiment of the fourth component shown in FIG. 9 in accordance with the principles of the present disclosure, the fifth component shown in FIG. 9, the sixth component shown in FIG. 9, and the seventh component shown in FIG. 9.

Portion 66 is an area of reduced wall thickness and can have a cross-section in the form of a notch creating a weakened zone. Portion 50 can have at least one flat surface 68 for the application of torque to setscrew 46. In some embodiments, surface 68 is on the exterior of portion 50. Portion 66 connects portion 50 and portion 52. Portion 66 is easily or readily ruptured, separated or broken when a pre-selected torque or force is applied. When portion 50 is removed, portion 52 remains as shown in FIGS. 10 and 11. An exemplary description of a setscrew having such a frangible portion is disclosed in U.S. Pat. No. 6,179,841 and U.S. patent application Ser. No. 12/609,728, which are each incorporated herein by reference, in their entireties.

System 20 includes one or a plurality of gauges, such as, for example, strain gauges 70 that is/are coupled to setscrew 46 to measure a force between setscrew 46 and rod 38 when setscrew 46 is engaged with head 24, as discussed herein. That is, thread form 54 is configured to engage thread form 44 to translate setscrew 46 relative to head 24 until setscrew 46 directly engages rod 38 within cavity 36 to fix rod 38 relative to head 24. Gauges 70 may each include one or more gauge s or gauge nodes that measure strain, force, resistance, load and or the like. References in the present specification to a gauge or sensor thereby disclose embodiments in which multiple gauges or sensors, respectively are used, and when multiple gauges/sensors are referenced in the present specification, various embodiments also include a single gauge or sensor. Gauges 70 measure the amount of force setscrew 46 exerts on rod 38, which are indicative of loading conditions of rod 38. For example, setscrew 46 may exert a first amount of force on rod 38 when system 20 is initially implanted within a patient. However, the amount of force setscrew 46 exerts on rod 38 may decrease over time for a variety of reasons. Such a decrease in the amount of force setscrew 46 exerts on rod 38 may indicate increased fusion of adjacent vertebrae, for example. Indeed, because the load on rod 38 is gradually transferred to bone as bone graft (e.g., autograft) heals, the load on the rod decreases over time.

As discussed herein, strain data from gauges 70 can provide an in vivo assessment of the bony incorporation of an autograft, for example, and thus the fusion of the autograft and vertebrae. For example, an expected pattern of strain detected by gauges 70 will initially involve large axial forces that will decrease over time as components of system 20, such as, for example, rod 38, share more of the load with the vertebrae that are being fused by the autograft. If the data from gauges 70 follows or deviates from the expected patterns, conclusions can be drawn about progress of the fusion between the autograft and the vertebrae. System 20 thus provides the ability to continuously, or on-demand, monitor fusion progress and biomechanical performance during the post-operative period by assessing strain data from gauges 70. Indeed, strain readings from gauges 70 may be used to develop an accurate, early assessment of the fracture healing rate and the potential for not uniting. An early diagnosis of delayed union is advantageous because it allows the surgeon to take remedial steps as soon as a possible non-union is suspected, thus prompting intervention. Because of this ability to continuously or on-demand monitor fusion progress and biomechanical performance, it may be possible to appropriately time, or even avoid, additional surgery. Further, information gathered from such in vivo assessments can lead to improvements in surgical techniques and spinal implant design.

Figures 4, 5:
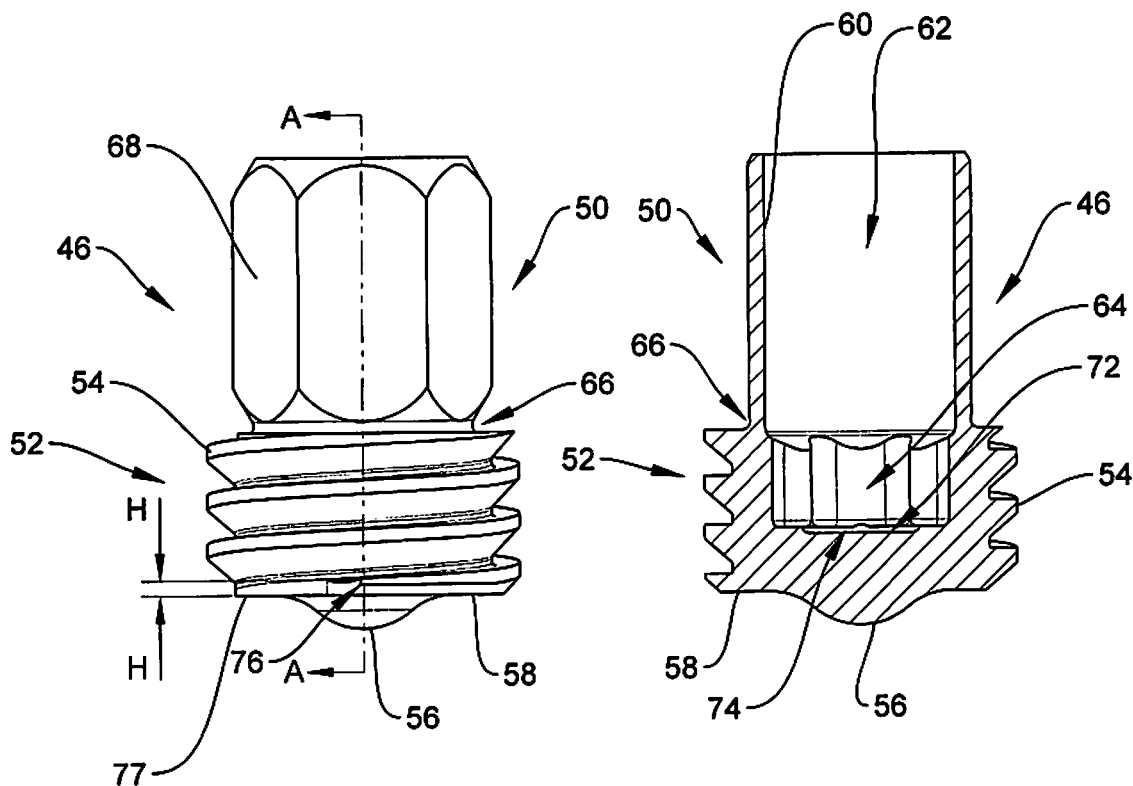
FIG. 4 is a side view of one embodiment of a second component of the system shown in FIG. 1, in accordance with the principles of the present disclosure.
FIG. 5 is a side, cross-sectional view of the component shown in FIG. 4 taken along lines A-A in FIG. 4.
Figure 6:
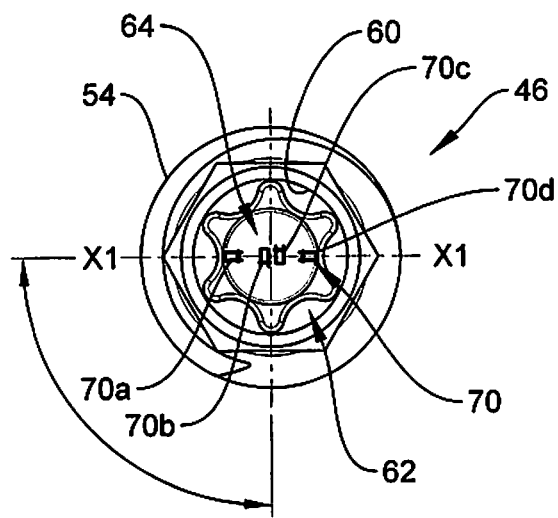
FIG. 6 is a top view of the second component shown in FIG. 4 and one embodiment of a third component of the system shown in FIG. 1, in accordance with the principles of the present disclosure.

Gauges 70 may be selectively positioned on setscrew 46 to measure a force between setscrew 46 and rod 38 when setscrew 46 is engaged with head 24. In some embodiments, gauges 70 are positioned in socket 62. In some embodiments, gauges 70 are positioned in recess 64. In some embodiments, gauges 70 directly engage a surface 72 of setscrew 46 that defines a groove 74 that is distal to recess 64, as shown in FIG. 5. Positioning gauges 70 in groove 74 prevents a bit of a driving tool from directly engaging gauges 70 when the bit is positioned in recess 64 so as not to deform or otherwise compromise gauges 70.

Figures 7, 8:
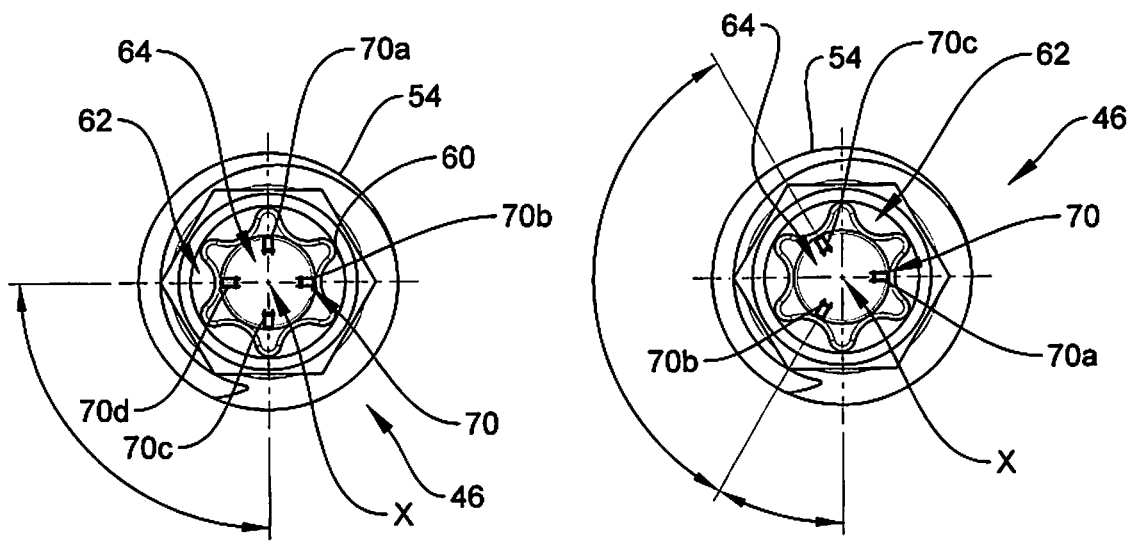
FIG. 7 is a top view of the second component shown in FIG. 4 and one embodiment of the third component of the system shown in FIG. 1, in accordance with the principles of the present disclosure.
FIG. 8 is a top view of the second component shown in FIG. 4 and one embodiment of the third component of the system shown in FIG. 1, in accordance with the principles of the present disclosure.

In some embodiments, gauges 70 are aligned linearly on setscrew 46. For example, in one embodiment, shown in FIG. 6, setscrew 46 includes a first gauge 70a, a second gauge 70b, a third gauge 70c and a fourth gauge 70d that are aligned along a transverse axis X1. It is envisioned that gauges 70 may also be positioned radially about setscrew 46. For example, in one embodiment, shown in FIG. 7, setscrew 46 includes a first gauge 70a, a second gauge 70b, a third gauge 70c and a fourth gauge 70d, wherein gauges 70a, 70b, 70c, 70d form a radial pattern, with gauges 70a, 70b, 70c, 70d each positioned 90 degrees from an adjacent one of gauges 70a, 70b, 70c, 70d. In one embodiment, shown in FIG. 8, setscrew 46 includes a first gauge 70a, a second gauge 70b and a third gauge 70c, wherein gauges 70a, 70b, 70c form a radial pattern, with gauges 70a, 70b, 70c each positioned 120 degrees from an adjacent one of gauges 70a, 70b, 70c. One angle indication in FIG. 8 shows the 120 degree relationship between adjacent gauges 70 and another angle indication in FIG. 8 shows an angle between one of gauges 70 and a vertical axis. In some embodiments, gauges 70a, 70b, 70c, 70d each include the same type of strain gauge. In some embodiments, at least one of gauges 70a, 70b, 70c, 70d is different than at least one other of gauges 70a, 70b, 70c, 70d. For example, in one embodiment, gauges 70a, 70d are radial strain gauges and gauges 70b, 70c are circumferential strain gauges. In some embodiments, two of gauges 70a, 70b, 70c, 70d are positioned in a radial direction and two of gauges 70a, 70b, 70c, 70d are positioned in a tangential direction. That is, two of gauges 70a, 70b, 70c, 70d are oriented about a radius of setscrew 46 and two of gauges 70a, 70b, 70c, 70d are positioned along a tangential line of setscrew 46.

Figure 2:
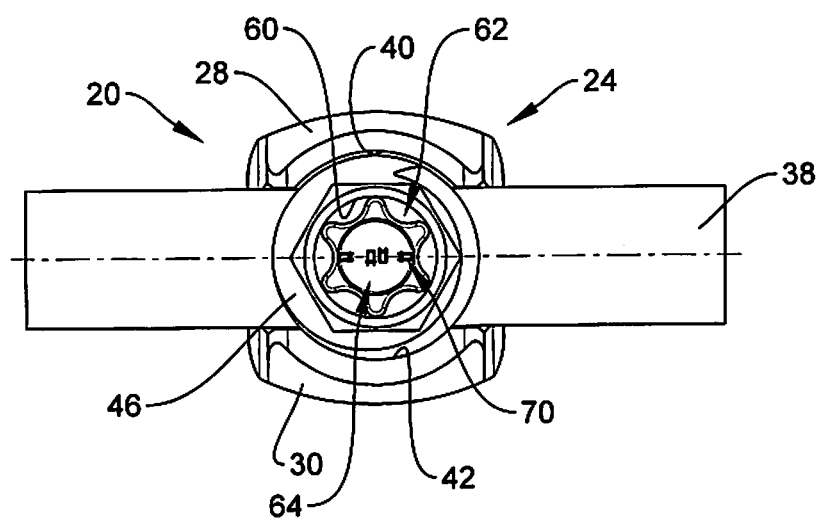
FIG. 2 is a top view of components of the system shown in FIG. 1.
Figure 3:
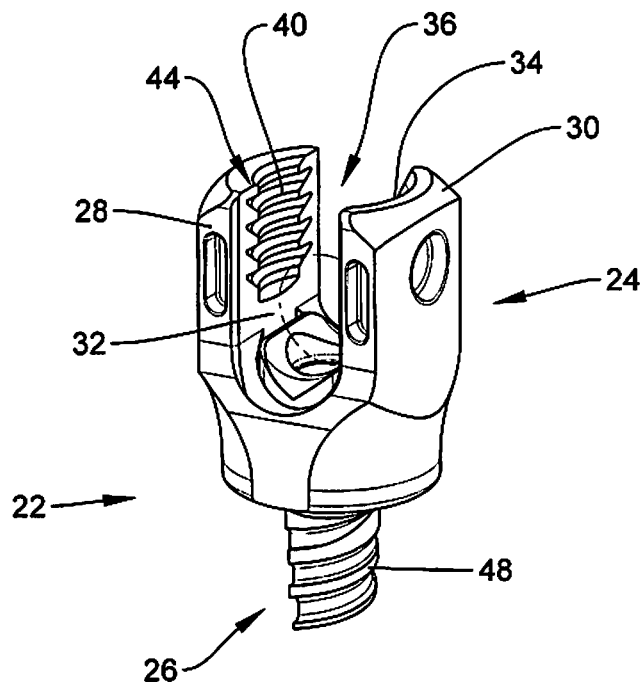
FIG. 3 is a perspective view of one embodiment of a first component of the system shown in FIG. 1, in accordance with the principles of the present disclosure.

Further regarding position of gauge(s) 70, there are benefits to controlling orientation of gauges 70. Doing so can result in more-accurate loading data. For example, in some embodiments, the orientation of gauges 70 must have a direct relationship to rod 38 when rod 38 is positioned in cavity 36. In one embodiment, the orientation of gauges 70 must be inline with rod 38 when rod 38 is positioned in cavity 36, as shown in FIG. 2. In one embodiment, the orientation of gauges 70 must be transverse to rod 38 when rod 38 is positioned in cavity 36. In one embodiment, the orientation of gauges 70 must be at an acute angle relative to rod 38 when rod 38 is positioned in cavity 36.

In order to position gauges 70 at a selected orientation relative to rod 38, thread form 54 is timed and/or clocked with thread form 44 such that gauges 70 will be positioned at the selected orientation relative to rod 38 when thread form 54 is fully threaded with thread form 44. In some embodiments, the timing and/or clocking of thread form 54 with thread form 44 is determined by the positioning of a start 76 of thread form 54 located at distal end 77. As shown in FIG. 4, distal end 77 includes height H that is a controlled dimension used to define the position and/or orientation of start 76. Start 76 is selectively positioned along thread form 54 such that gauges 70 will be positioned at the selected orientation relative to rod 38 when thread form 54 is fully threaded with thread form 44. In some embodiments, setscrew 46 is prevented from being rotated relative to head 24 in a rotational direction, such as, for example, clockwise, when thread form 54 is fully threaded with thread form 44. In some embodiments, start 76 is selectively positioned along thread form 54 such that gauges 70 will be positioned at the selected orientation relative to rod 38 when thread form 54 is fully tightened with thread form 44. In some embodiments, start 76 is selectively positioned along thread form 54 such that gauges 70 will be positioned at the selected orientation relative to rod 38 when setscrew 46 is prevented from translating axially in one direction relative to head 24 by rod 38. That is, gauges 70 will be positioned at the selected orientation relative to rod 38 when tip 56 first engages rod 38 such that rod 38 is fixed relative to head 24.

In some embodiments, system 20 includes one or more components that allow gauges 70 to send and/or analyze the measurements from gauges 70 relating to force between setscrew 46 and rod 38. For example, in one embodiment, shown in FIGS. 9-12, a load-sensing assembly 78 includes an antenna 80, such as a radio frequency identification (RFID) coil, a near field-communication (NFC) antenna or other short-range communication transmitter and/or receiver. In some embodiments, assembly 78 includes one or more integrated circuits 82 such as, for example, an RFID chip or an NFC chip. In some embodiments, assembly 78 includes one or more electronics components 84 and gauges 70. In some embodiments, assembly 78 is the same or similar to the load sensing assembly disclosed in U.S. Ser. No. 16/039,592, which is expressly incorporated herein by reference, in its entirety.

Figure 9:
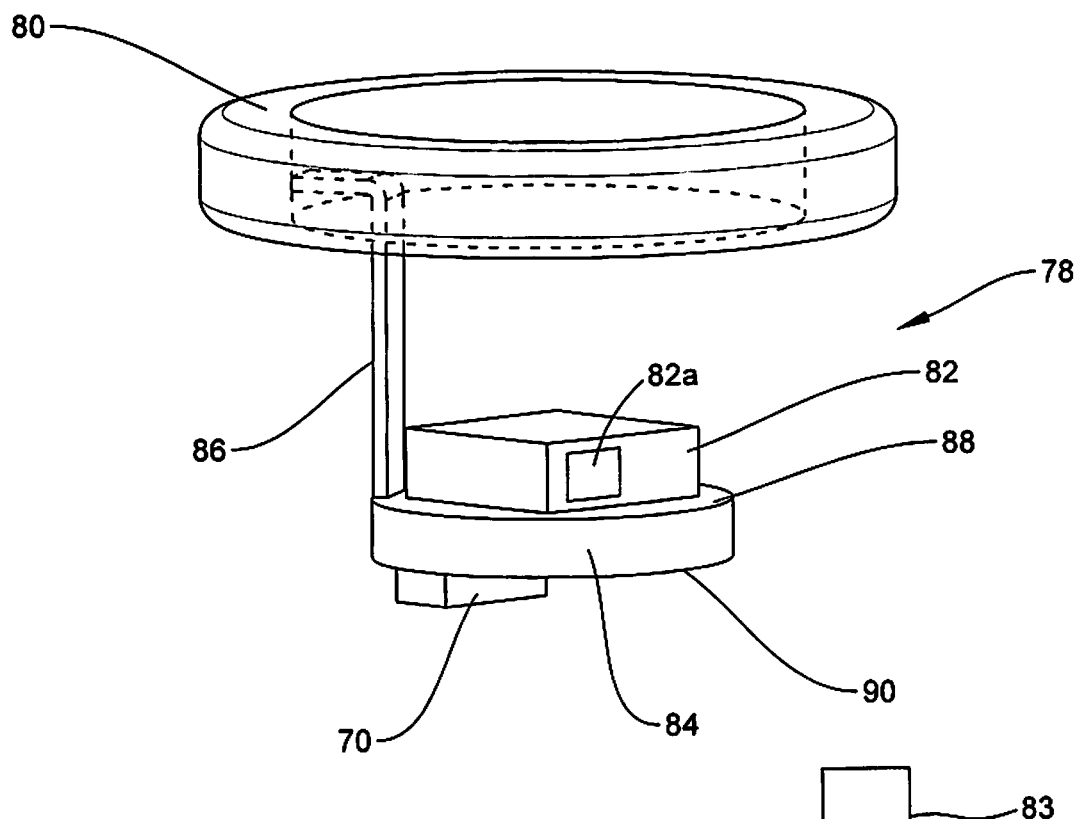
FIG. 9 is a perspective view of one embodiment of the third component of the system shown in FIG. 1, one embodiment of a fourth component of the system shown in FIG. 1, one embodiment of a fifth component of the system shown in FIG. 1, one embodiment of a sixth component of the system shown in FIG. 1, and one embodiment of a seventh component of the system shown in FIG. 1, in accordance with the principles of the present disclosure.

In some embodiments, electronics components 84 include a flexible electronics component, such as, for example, a flex circuit or one or more electrical circuits. In some embodiments, antenna 80 may be operably connected to electronics component 84 via a connecting member 86. For example, as shown in FIG. 9, member 86 may be connected to both antenna 80 and electronics component 84. In some embodiments, member 86 is positioned perpendicularly to both antenna 80 and electronics component 84. In some embodiments, member 86 and antenna 80 may be constructed integrally or may be separately constructed and attached together in any suitable manner, such as for example by adhesive, chemical, mechanical or cement bonding. In some embodiments, member 86 and electronics component 84 may be constructed integrally or may be separately constructed and attached together in any suitable manner, such as for example by adhesive, chemical, mechanical or cement bonding.

In some embodiments, circuit 82 is operably connected to electronics component 84. As shown in FIG. 9, electronics component 84 may have a top surface 88 and a bottom surface 90. Circuit 82 may be positioned on surface 88 of electronics component 84, and may be connected to surface 88 in any suitable manner, including, for example, adhesive, chemical, mechanical or cement bonding. Circuit 82 may include a memory 82a according to an embodiment. Memory 82a may be used to store various information. For example, one or more measurements of one or more of gauges 70 may be stored in memory 82a. In some embodiments, a unique identifier associated with assembly 78, a component thereof, or setscrew 46 may be stored in memory 82a. Additional and/or alternate information or types of information may be stored according to this disclosure.

In some embodiments, one or more of gauges 70 may be operably connected, for example by adhesive, cement, mechanical or chemical bonding, to electronics component 84. For example, one or more of gauges 70 may be operably connected to electronics component 84 via surface 90 of electronics component 84. One or more of gauges 70 may be connected to surface 90 of electronics component 84 in any suitable manner including, without limitation, via an adhesive bonding agent.

Figure 12:
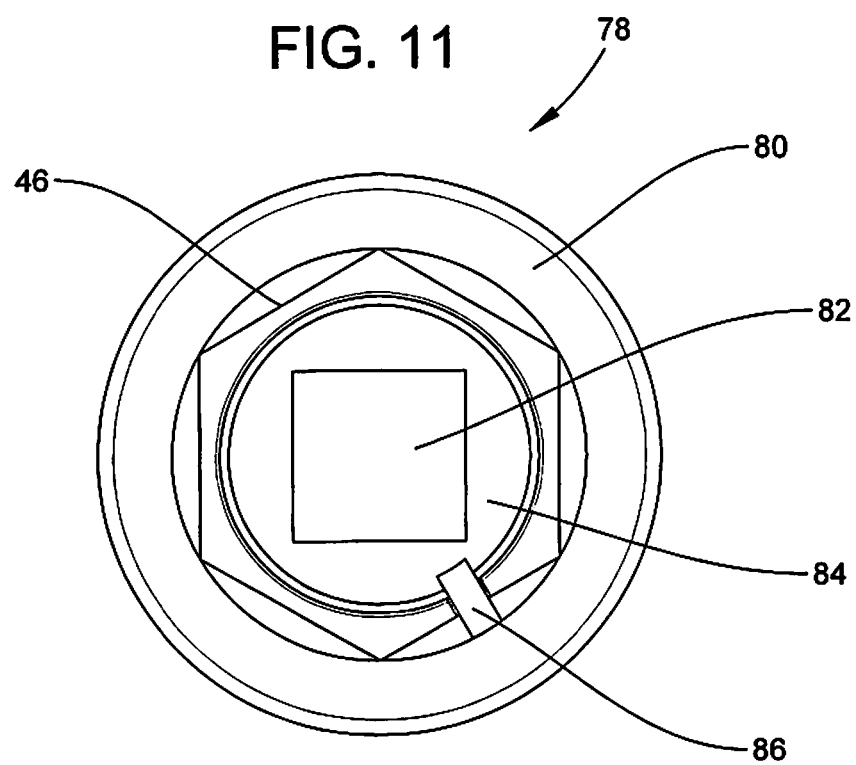
FIG. 12 is a top view of the second component shown in FIG. 4, the third component shown in FIG. 9, the fourth component shown in FIG. 9, the fifth component shown in FIG. 9, the sixth component shown in FIG. 9, and the seventh component shown in FIG. 9.

As shown in FIG. 9, antenna 80 may have a generally curved shape. Antenna 80 may include a first end and a second end. Antenna 80 may include an opening that extends from the first end toward the second end, as shown in FIG. 9. As shown in FIG. 10, assembly 78 may be configured to be mounted to setscrew 46. Antenna 80 is sized to extend around setscrew 46 such that circuit 82, electronics component 84, gauges 70 and member 86 are positioned within socket 62, recess 64 and/or groove 74. Antenna 80 may circumferentially surround at least a portion of the exterior of setscrew 46. In one embodiment, shown in FIG. 11, antenna 80 may be positioned at least partially inside of socket 62. In some embodiments, gauges 70 may be connected to setscrew 46 in any suitable manner including, without limitation via an adhesive. FIG. 12 illustrates a top view of assembly 78 mounted to setscrew 46.

In various contemplated embodiments, any activity described herein can be performed by a specially configured computer, or system or network of computers. Activities can performed by the computing device or system based on any of various input, including from one or more implanted gauges and one or more of the readers or smart tools or instruments described herein. The computing device or system can process, in performing the activities, big data or other information, such as profile or historic diagnostics data, about a subject patient and/or any number of other patients or persons. Example computing activities include but are not limited to: (i) collecting, organizing, or otherwise processing data received; (ii) monitoring gauge or patient status, (iii) transmitting alerts, notifications, or data, received or processed, to any desired destination (to, e.g., patient or hospital device) for consideration or further use; (iv) determining patterns in gauge or patient changes of state, or adherence to patterns; and (v) diagnostics.

In various contemplated embodiments, the specially configured computer, or system or network of computers is/are configured to provide diagnostic feedback. In some embodiments, the specially configured computer, system or network of computers communicate(s) with coils located outside a patient for powering electronic components of system 20, such as, for example, gauges 70. In some embodiments, the specially configured computer, system or network of computers communicate(s) with electronic components that provide remote power options using telemetry, such as, for example, NFC. In some embodiments, the electronic components include a NFC power harvesting integrated circuit. In some embodiments, the electronic components include an analog front end integrated circuit. In some embodiments, the electronic components include a microprocessor integrated circuit. In some embodiments, the electronic components are configured to provide diagnostic feedback to guide and/or determine an optimum location for an external coil for powering components of system 20, such as, for example, gauges 70. In some embodiments, the electronic components include resonant circuits that provide an auto tuning feature to optimize communication between components of system 20, such as, for example, gauges 70, and the remote power source. In some cases, various factors may contribute to detuning a resonant circuit, for example, implant depth, metal in the vicinity both inside and outside a body, and/or other factors. In some embodiments, the electronic components have an auto tuning feature and/or method that includes changing a tuning capacitor value and/or shifting operating frequency+/− over a range relative to a selected frequency. In some embodiments, the external coil and associated circuitry includes an auto tuning feature to optimize communication between the electronic components and the remote power source, and/or other components of system 20.

In some embodiments, the NFC device remotely communicates with a device, such as, for example, a computer that is disposed outside or external to the patient's body to transfer, transmit and/or receive data relating to gauges 70. Gauges 70 may include diagnostic sensor electronics connected with one or more sensors. The diagnostic sensor electronics may comprise various commercially available integrated circuit devices, see, for example, but not limited to, the AD5933 Impedance Converter Network Analyzer distributed by Analog Devices. The integrated circuit device may comprise various commercially available integrated circuit devices, see, for example, but not limited to, the RF430 microcontroller distributed by Texas Instruments RF430.

In some embodiments, the diagnostic sensor electronics and/or the analog device gather information from gauges 70, such as, for example, loading information, pressure information, tension information, motion information, alignment or misalignment information and/or temperature, relating to one or more components of system 20, as described herein. The computer remotely communicates with the NFC device, as described herein, to collect data from gauges 70 via the diagnostic sensor electronics. In some embodiments, a reader communicates with the computer. The reader emits a small electric current that creates a magnetic field to bridge the physical space between the reader and gauges 70. The electric field is received by the NFC device and converted into electrical impulses to communicate data and diagnostics, relating to gauges 70 to the computer, as described herein.

The diagnostic sensor electronics provides feedback and/or measure one or more diagnostic conditions. The diagnostic sensor electronics sense and transmit to the computer various diagnostic indicia, and in some embodiments, diagnose and respond to such measurements, such as, for example, in the context of a spinal implant surgery. In some embodiments, a surgeon can monitor a patient after surgery, and make adjustments to one or more components of system 20. In some embodiments, this configuration allows one or more components of system 20 to be corrected or modified based on changes that take place subsequent to surgery, and/or for selected and remote changes to diagnostic conditions inside the patient's body. In some embodiments, the diagnostic sensor electronics indicate a fusion rate of vertebrae. In some embodiments, one or more measurements obtained by one or more of gauges 70 may be stored by circuit 82 of assembly 78, such as, for example, in memory 82a of circuit 82. Circuit 82 may be interrogated by a reader 83. For example, an RFID chip may be read by an RFID reader. As another example, an NFC chip of circuit 82 may be read by or may otherwise communicate with an NFC reader or other NFC-enabled device. A reader may interrogate circuit 82 when in a certain proximity to circuit 82. In some embodiments, a reader may interrogate circuit 82 after circuit 82 has been implanted into a patient within setscrew 46. In some embodiments, circuit 82 may communicate with a reader or other electronic device without being interrogated.

Circuit 82 may transmit one or more measurements to the reader. This transmission may occur in response to being interrogated by the reader, or the transmission may be initiated by circuit 82. The reader may receive the transmitted measurements, and may cause at least a portion of the measurements to be displayed to a user. For example, a physician may use a reader to interrogate an RFID chip of a patient's implant, such as, for example bone screw 22, rod 38 or setscrew 46. The reader may include a display, or may be in communication with a display device, which may display at least a portion of the measurements received from the RFID chip.

In some embodiments, circuit 82 is passive such that the chip has no internal power source and is powered by the energy transmitted from a reader. In such embodiments, circuit 82 may not transmit information until interrogated by a reader. In some embodiments, circuit 82 may be active such that the chip is battery-powered and capable of broadcasting its own signal. Active circuit 82 may transmit information in response to be interrogated by a reader, but also on its own without being interrogated. For example, active circuit 82 may broadcast a signal that contains certain information such as, for example, one or more measurements gathered by one or more of gauges 70. Active circuit 82 may continuously broadcast a signal, or it may periodically broadcast a signal. Power may come from any number of sources, including, for example, thin film batteries with or without encapsulation or piezo electronics.

In some embodiments, one or more sensors of gauges 70 may transmit information by directly modulating a reflected signal, such as an RF signal. The sensors of gauges 70 may form a Wireless Passive Sensor Network (WPSN), which may utilize modulated backscattering (MB) as a communication technique. External power sources, such as, for example, an RF reader or other reader, may supply a WPSN with energy. The sensor(s) of the WPSN may transmit data by modulating the incident signal from a power source by switching its antenna impedance.

One or more measurements received from assembly 78 may be used to make determinations of the condition of a spinal implant and/or treatment of a spinal disorder. For instance, proper placement of rod 38 and/or setscrew 46 may result in an acceptable range of force measurements collected by gauges 70. Measurements outside of this range may indicate a problem with the placement or positioning of rod 38 and/or setscrew 46, such as, for example, loosening of setscrew 46, failure or rod 38, yield or fracture/breakage, improper torque, breakage of the bone segment or portion, the occurrence of fusion or amount of fusion, and/or the like.

One or more tools or instruments may include a reader which may be used to gather information from circuit 82 during or in connection with a procedure. For instance, a torque tool may be used to loosen or tighten setscrew 46. A torque tool may include a reader, or may be in communication with a reader, such that a user of the torque tool is able to obtain, in substantially real time, one or more measurements relating to setscrew 46 and rod 38 placement that are measured by gauges 70 via the tool. For example, as a user is applying torque to setscrew 46, the user may see one or more force measurements between setscrew 46 and rod 38 in order to determine that the positioning of setscrew 46 and/or rod 38 is correct and that the proper force is being maintained. In some embodiments, a tool or instrument may include a display device on which one or more measurements may be displayed. In some embodiments, a tool or instrument may be in communication with a display device, and may transmit one or more measurements for display on the display device via a communications network.

In some embodiments, an electronic device, such as a reader or an electronic device in communication with a reader, may compare one or more measurements obtained from circuit 82 to one or more acceptable value ranges. If one or more of the measurements are outside of an applicable value range, the electronic device may cause a notification to be made. For example, an electronic device may generate an alert for a user, and cause the alert to be displayed to the user via a display device. Alternatively, an electronic device may send an alert to a user such as via an email message, a text message or otherwise.

In some embodiments, circuit 82 may store a unique identifier associated with setscrew 46. Circuit 82 may transmit the unique identifier to an electronic device. For example, when a reader interrogates circuit 82, circuit 82 may transmit a unique identifier for setscrew 46 that is stored by circuit 82 to the reader. Having access to a unique identifier for setscrew 46 may help a user ascertain whether the measurements that are being obtained are associated with setscrew 46. Also, having access to a unique identifier for setscrew 46 may help a user take inventory of one or more components. For instance, after spinal surgery, a physician or other health care professional may use a reader to confirm that all of the setscrews allocated for the procedure have been used and are positioned in a patient.

In assembly, operation and use, surgical system 20, similar to the systems and methods described herein, is employed with a surgical procedure for treatment of a spinal disorder affecting a section of a spine of a patient, as discussed herein. The components of surgical system 20 are employed with a surgical procedure for treatment of a condition or injury of an affected section of the spine, such as, for example, vertebrae.

In use, to treat a selected section of vertebrae, a medical practitioner obtains access to a surgical site in any appropriate manner, such as through incision and retraction of tissues. In some embodiments, surgical system 20 can be used in any existing surgical method or technique including open surgery, mini-open surgery, minimally invasive surgery and percutaneous surgical implantation, whereby vertebrae are accessed through a mini-incision, or sleeve that provides a protected passageway to the area. Once access to the surgical site is obtained, the particular surgical procedure can be performed for treating the spine disorder.

An incision is made in the body of a patient and a cutting instrument creates a surgical pathway for implantation of components of surgical system 20. A preparation instrument can be employed to prepare tissue surfaces of vertebrae as well as for aspiration and irrigation of a surgical region. A pilot hole is made in a vertebra for receiving shaft 26. Shaft 26 is positioned in the pilot hole and is rotated relative to the vertebra using a driver, for example, such that thread form 48 directly engages tissue to drive shaft 26 into to the vertebra. Shaft 26 may be driven into the vertebrae a selected amount to fix shaft 26 relative to the vertebra. Once shaft 26 is sufficiently fixed relative to the vertebra, head 24 is connected with shaft 26. In some embodiments, head 24 is configured to snap onto shaft 26 to prevent head 24 from unintentionally being removed from shaft 26. A spinal construct, such as, for example, rod 38 is inserted into cavity 36. Once rod 38 is positioned in cavity 36, thread form 54 is aligned with thread form 44 and setscrew 46 is rotated relative to head 24 in a rotational direction, such as, for example, clockwise such that thread form 54 engages thread form 44. Further rotation of setscrew 46 relative to head 24 causes setscrew 46 to translate relative to head 24 such that tip 56 moves toward rod 38. Setscrew 46 is rotated relative to head 24 until tip 56 directly engages rod 38 and/or thread form 54 is fully threaded with thread form 44. Because thread form 54 is timed and/or clocked with thread form 44 to position gauges 70 at a selected orientation relative to rod 38 when rod 38 is positioned in cavity 36, gauges 70 will be positioned at the selected orientation relative to rod 38 when tip 56 directly engages rod 38 and/or thread form 54 is fully threaded with thread form 44.

One or more measurements obtained by gauges 70 are stored by circuit 82 of assembly 78, such as, for example, in memory 82a of circuit 82. In some embodiments, circuit 82 is interrogated by a reader to transmit the measurements obtained by gauges 70 to the reader. For example, an RFID chip of circuit 82 may be read by an external RFID reader. Alternatively, an NFC chip of circuit 82 may be read or otherwise communicate with an external NFC reader or other NFC-enabled device. In some embodiments, the reader interrogates circuit 82 when the reader is within a certain distance of circuit 82 to transmit the measurements obtained by gauges 70 to the reader. In some embodiments, circuit 82 may to transmit the measurements obtained by gauges 70 to the reader without the reader being interrogated. The reader can cause one or more of the measurements obtained by gauges 70 to be displayed on the reader itself or a separate display, such as, for example, a computer monitor.

The measurements obtained by gauges 70 are displayed to provide an in vivo assessment of the bony incorporation of an autograft, for example, and thus the fusion of the autograft and vertebrae. In some embodiments, the measurements obtained by gauges 70 are compared with an expected pattern of strain. If the data from gauges 70 follows or deviates from the expected patterns, conclusions can be drawn about progress of the fusion between the autograft and the vertebrae. In some embodiments, a surgeon may perform one or more procedures to improve the fusion between the autograft and the vertebrae, based on the in vivo assessment. In that gauges 70 may be configured to continuously provide measurements that can be read and displayed, system 20 thus provides the ability to continuously, or on-demand, monitor fusion progress and biomechanical performance during the post-operative period by assessing strain data from gauges 70. Indeed, strain readings from gauges 70 may be used to develop an accurate, early assessment of the fracture healing rate and the potential for not uniting. An early diagnosis of delayed union is advantageous because it allows the surgeon to take remedial steps as soon as a possible non-union is suspected, thus prompting intervention. Because of this ability to continuously or on-demand monitor fusion progress and biomechanical performance, it may be possible to appropriately time, or even avoid, additional surgery.

Upon completion of a procedure, as described herein, the surgical instruments, assemblies and non-implanted components of surgical system 20 are removed and the incision(s) are closed. One or more of the components of surgical system 20 can be made of radiolucent materials such as polymers. Radiomarkers may be included for identification under x-ray, fluoroscopy, CT or other imaging techniques. In some embodiments, surgical system 20 may include one or a plurality of spinal rods, plates, connectors and/or bone fasteners for use with a single vertebral level or a plurality of vertebral levels.

In some embodiments, one or more bone screws, as described herein, may be engaged with tissue in various orientations, such as, for example, series, parallel, offset, staggered and/or alternate vertebral levels. In some embodiments, one or more of the bone screws may comprise multi-axial screws, sagittal adjusting screws, pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

In one embodiment, surgical system 20 includes an agent, which may be disposed, packed, coated or layered within, on or about the components and/or surfaces of surgical system 20. In some embodiments, the agent may include bone growth promoting material, such as, for example, bone graft to enhance fixation of the components and/or surfaces of surgical system 20 with vertebrae. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal construct comprising:
   a spinal rod;
   a setscrew comprising an upper portion and a lower portion, the lower portion having a tip, the setscrew defining a socket extending through the upper portion and into the lower portion; and
   an assembly comprising:
     an electronics component having opposite upper and lower sides,
     a gauge coupled to the lower side of the electronics component such that the gauge is positioned in the socket, the gauge being configured to measure a force between the setscrew and the spinal rod when the tip engages the spinal rod,
     a circuit coupled to the upper side of the electronics component, the circuit being configured to store measurements obtained by the gauge,
     a member coupled to the upper side of the electronics component, and
     a ring-shaped antenna coupled to the member such that a portion of the antenna engages the upper portion of the setscrew and circumferentially surrounds at least a portion of an exterior of the setscrew.

2. The spinal construct recited in claim 1, wherein the exterior is an outer surface of the setscrew that defines a thread form and the setscrew comprises an opposite inner surface defining the socket.

3. The spinal construct recited in claim 1, wherein the exterior is an outer surface of the setscrew that defines a thread form and the setscrew comprises an opposite inner surface defining the socket, the gauge being coupled to the inner surface.

4. The spinal construct recited in claim 1, wherein the gauge comprises a plurality of gauges arranged along a transverse axis of the setscrew.

5. The spinal construct recited in claim 1, wherein the gauge comprises a plurality of gauges arranged radially about a longitudinal axis of the setscrew.

6. The spinal construct recited in claim 1 wherein the circuit is an integrated circuit that is in communication with the antennae and the gauge.

7. The spinal construct recited in claim 1, wherein the setscrew extends along a central longitudinal axis between the upper portion and the lower portion, the setscrew comprising an inner surface and an outer surface defining the exterior, the inner surface defining the socket, the socket extending parallel to the central longitudinal axis.

8. The spinal construct recited in claim 7, wherein the outer surface defines a plurality of flat surfaces extending along the upper portion, the flat surfaces being positioned radially about the central longitudinal axis.

9. The spinal construct recited in claim 7, wherein the socket is coaxial with the central longitudinal axis.

10. The spinal construct recited in claim 7, wherein the outer surface defines a thread form extending along the lower portion.

11. A spinal construct comprising:
    a first member comprising a cavity and a first mating surface;
    a second member disposed in the cavity;
    a third member comprising an upper portion and a lower portion, the third member having a second mating surface, a tip and a socket, the second mating surface being configured for engagement with the first mating surface to couple the third member to the first member; and
    an assembly comprising:
      an electronics component having opposite upper and lower sides,
      a gauge coupled to the lower side of the electronics component such that the gauge is positioned in the socket, the gauge being configured to measure a force between the third member and the second member when the second mating surface is coupled to the first mating surface and the tip engages the second member,
      a circuit coupled to the upper side of the electronics component, the circuit being configured to store measurements obtained by the gauge,
      a member coupled to the upper side of the electronics component, and a ring-shaped antenna coupled to the member such that a portion of the antenna engages the upper portion of the third member and circumferentially surrounds at least a portion of an exterior of the third member.

12. The spinal construct recited in claim 11, wherein the first mating surface is a first thread form and the second mating surface is a second thread form.

13. The spinal construct recited in claim 11, wherein the first mating surface is a first thread form and the second mating surface is a second thread form, the second thread form being timed with the first thread form to position the gauge in a selected orientation relative to the second member.

14. The spinal construct recited in claim 11, wherein the third member extends along a central longitudinal axis between the upper portion and the lower portion, the third member comprising an inner surface and an outer surface defining the exterior, the inner surface defining the socket, the socket extending parallel to the central longitudinal axis.

15. The spinal construct recited in claim 14, wherein the outer surface defines a plurality of flat surfaces extending along the upper portion, the flat surfaces being positioned radially about the central longitudinal axis.

16. The spinal construct recited in claim 14, wherein the socket extends through the upper portion and into the lower portion, the socket being coaxial with the central longitudinal axis.

17. The spinal construct recited in claim 14, wherein the first mating surface is a first thread form and the second mating surface is a second thread form extending outwardly from the outer surface, the second thread form extending along the lower portion.

18. A spinal construct comprising:
a bone fastener comprising a cavity and a first mating surface;
a rod disposed in the cavity;
a setscrew comprising an upper portion and a lower portion, the setscrew comprising a second mating surface, a tip and a socket, the second mating surface being configured for engagement with the first mating surface to couple the setscrew to the bone fastener; and
an assembly comprising:
an electronics component having opposite upper and lower sides,
a gauge coupled to the lower side of the electronics component such that the gauge is positioned in the socket, the gauge being configured to measure a force between the setscrew and the rod when the setscrew is coupled to the bone fastener and the tip engages the rod,
a member coupled to the upper side of the electronics component, and
a ring-shaped antenna coupled to the member such that a portion of the antenna engages the upper portion of the setscrew and circumferentially surrounds at least a portion of an exterior of the setscrew,
wherein the setscrew extends along a central longitudinal axis between the upper portion and the lower portion, the setscrew comprising an inner surface and an outer surface, the inner surface defining the socket, the socket extending parallel to the central longitudinal axis.

* * * * *